(12) United States Patent
Walker et al.

(10) Patent No.: US 6,449,326 B1
(45) Date of Patent: Sep. 10, 2002

(54) APPARATUS AND METHOD FOR ULTRASONICALLY EXAMINING REMOTELY LOCATED WELDS IN CAST STAINLESS STEEL NUCLEAR STEAM SUPPLY SYSTEMS

(75) Inventors: Stanley Maurice Walker; Steven Allen Kenefick; Robert Jeffery Lowery, all of Charlotte, NC (US); Adam Roy Caban, Columbia, SC (US)

(73) Assignee: Electric Power Research Institute, Inc., Palo Alto, CA (US)

( * ) Notice: Subject to any disclaimer, the term of this patent is extended or adjusted under 35 U.S.C. 154(b) by 2 days.

(21) Appl. No.: 09/650,114

(22) Filed: Aug. 29, 2000

Related U.S. Application Data

(63) Continuation of application No. 09/074,335, filed on May 7, 1998, now Pat. No. 6,215,836.

(51) Int. Cl.[7] ............................................. G21C 17/017
(52) U.S. Cl. ...................... 376/260; 376/245; 376/249; 73/584; 73/623; 73/633; 73/634; 73/640; 324/220
(58) Field of Search ................................ 376/245, 249, 376/260; 73/584, 623, 633, 640, 634; 324/220

(56) References Cited

U.S. PATENT DOCUMENTS

| | | | | |
|---|---|---|---|---|
| 3,417,609 A | * | 12/1968 | Graham | 73/633 |
| 3,460,028 A | * | 8/1969 | Beaver et al. | 324/37 |
| 3,508,436 A | * | 4/1970 | Krautkramer | 73/640 |
| 3,600,613 A | | 8/1971 | Clarke | 73/67.8 |
| 3,786,684 A | * | 1/1974 | Wiers et al. | 73/432 R |
| 3,868,847 A | * | 3/1975 | Gunkel | 73/67.8 S |
| 4,037,465 A | * | 7/1977 | Cook et al. | 73/67.8 S |
| 4,131,018 A | * | 12/1978 | Muller et al. | 73/432 R |
| 4,304,134 A | * | 12/1981 | Rouse et al. | 73/634 |
| 4,368,644 A | * | 1/1983 | Wentzell et al. | 73/634 |
| 4,460,920 A | * | 7/1984 | Weber et al. | 358/100 |
| 4,581,938 A | * | 4/1986 | Wentzell | 73/623 |
| 4,586,380 A | * | 5/1986 | Patterson | 73/623 |
| 4,757,258 A | | 7/1988 | Kelly, Jr. et al. | 324/220 |
| 4,843,896 A | * | 7/1989 | Napeloni et al. | 73/866.5 |
| 5,046,364 A | * | 9/1991 | Stasuk et al. | 73/623 |
| 5,077,907 A | * | 1/1992 | Furr | 33/529 |
| 5,156,803 A | * | 10/1992 | Engding et al. | 376/249 |
| 5,189,915 A | * | 3/1993 | Reinhart et al. | 73/623 |
| 5,254,944 A | | 10/1993 | Hemes et al. | 324/220 |
| 5,272,734 A | | 12/1993 | Clark et al. | 376/260 |
| 5,285,689 A | * | 2/1994 | Hapstack et al. | 73/623 |
| 5,335,546 A | * | 8/1994 | Karbach et al. | 73/622 |
| 5,460,045 A | | 10/1995 | Clark et al. | 73/622 |
| 5,479,100 A | * | 12/1995 | Fowler et al. | 324/263 |
| 5,574,223 A | * | 11/1996 | Kiefer | 73/623 |
| 5,641,909 A | * | 6/1997 | Kiefer et al. | 73/623 |
| 5,987,991 A | * | 11/1999 | Trantow et al. | 73/624 |
| 6,076,407 A | * | 6/2000 | Levesque et al. | 73/623 |

* cited by examiner

*Primary Examiner*—Michael J. Carone
*Assistant Examiner*—Jack Keith
(74) *Attorney, Agent, or Firm*—Dorsey & Whitney LLP

(57) ABSTRACT

An apparatus for ultrasonically examining a weld in a nuclear steam supply system includes an elongated guide rod for positioning within a pipe of the nuclear steam supply system. An ultrasonic transducer is positioned at an end of the elongated guide rod. A collapsible shoe encloses the ultrasonic transducer. The collapsible shoe includes a biasing mechanism to allow the collapsible shoe to pass through the pipe while the pipe is at a first circumference and while the pipe is at a second circumference. The collapsible shoe continuously contacts the pipe to establish ultrasonic coupling for the ultrasonic transducer.

10 Claims, 4 Drawing Sheets

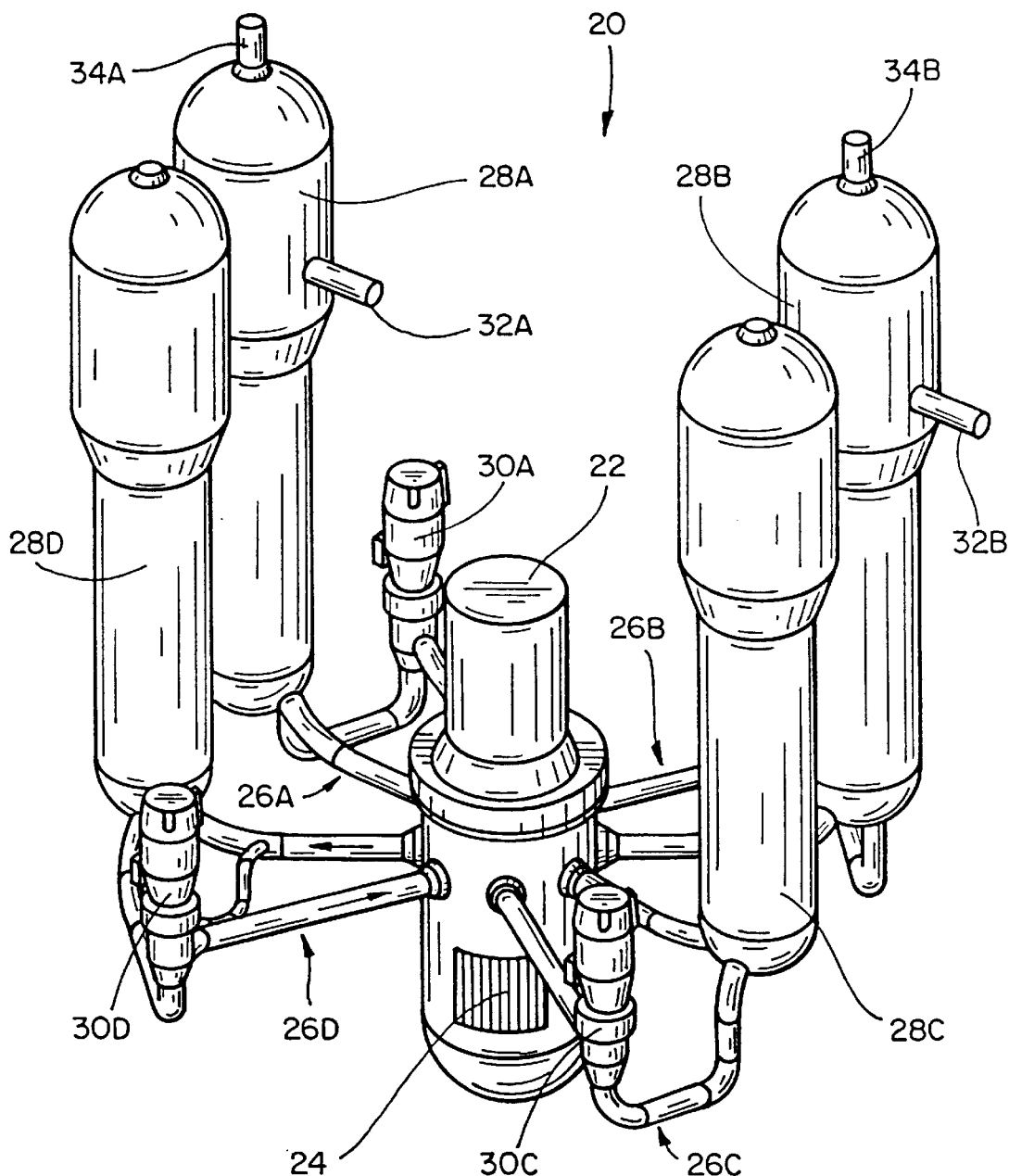
FIG_1
(PRIOR ART)

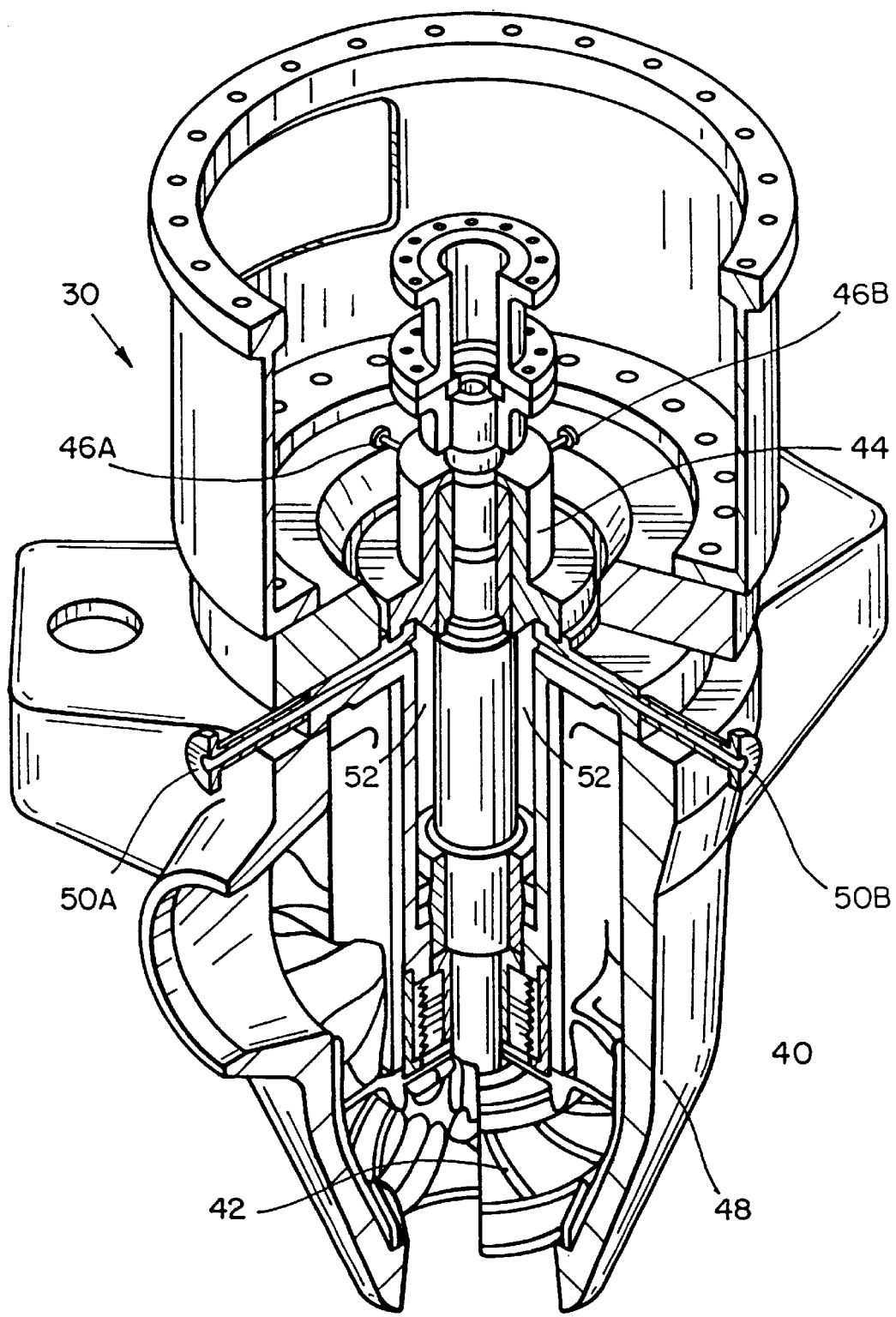
FIG_2
(PRIOR ART)

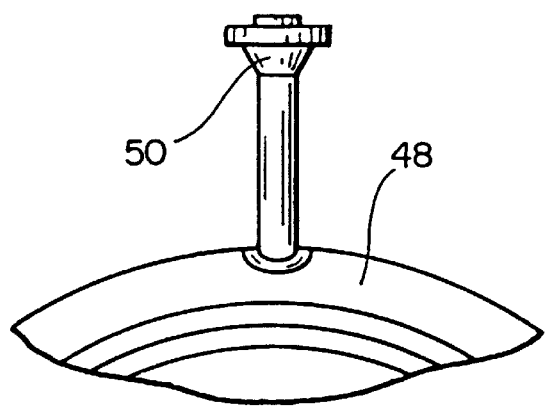
FIG_3
(PRIOR ART)
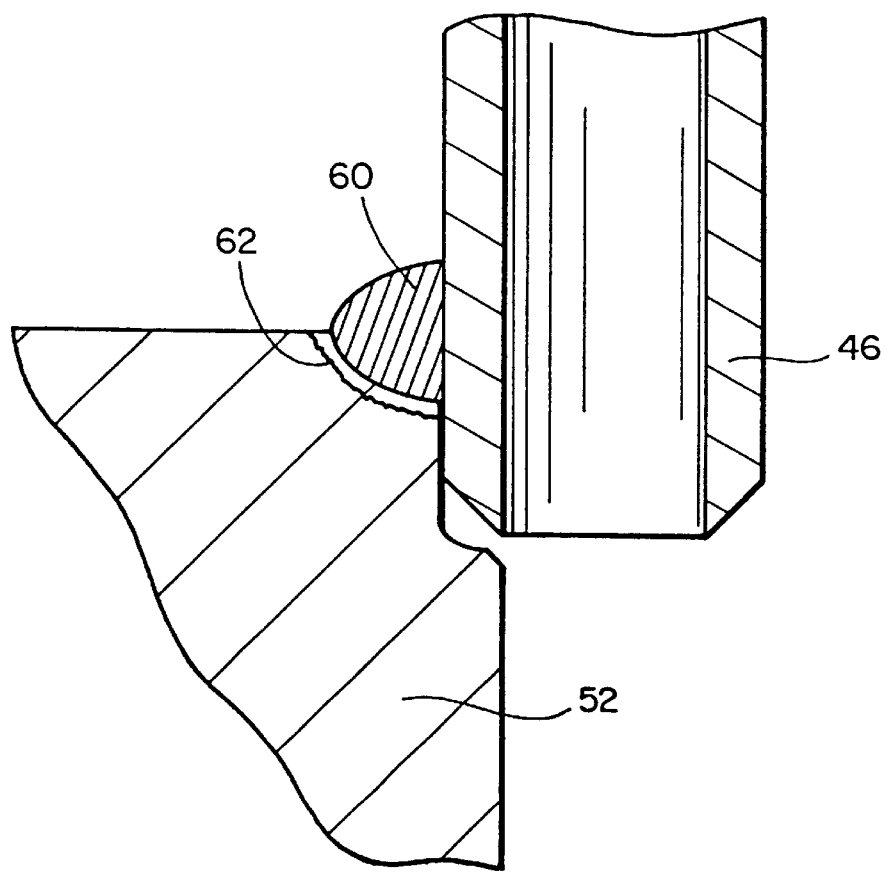
FIG_4
(PRIOR ART)

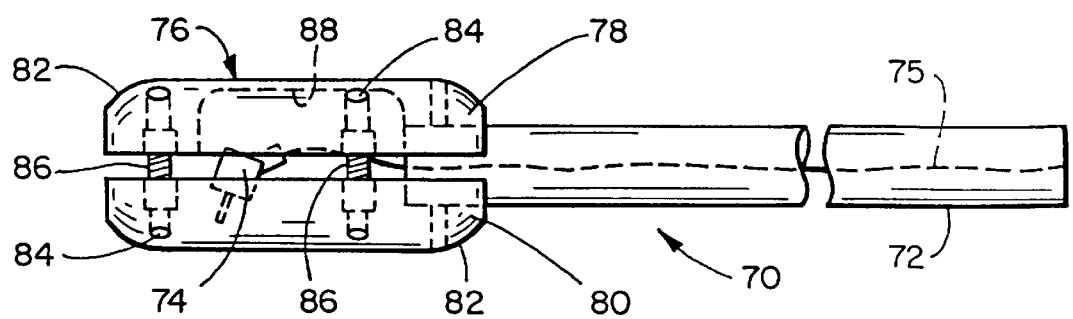
FIG_5
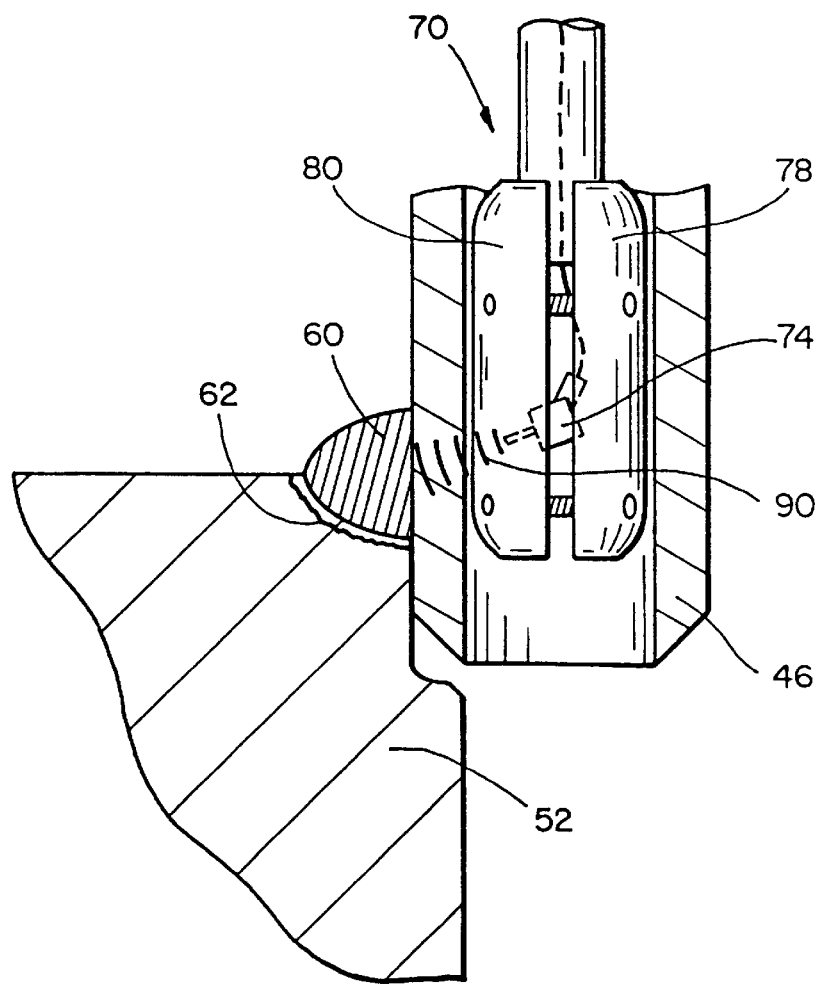
FIG_6

APPARATUS AND METHOD FOR ULTRASONICALLY EXAMINING REMOTELY LOCATED WELDS IN CAST STAINLESS STEEL NUCLEAR STEAM SUPPLY SYSTEMS

This application is a continuation of Ser. No. 09/074,335 filed May 7, 1998, now U.S. Pat. No. 6,215,836.

BRIEF DESCRIPTION OF THE INVENTION

This invention relates generally to the maintenance of nuclear steam supply systems. More particularly, this invention relates to a technique of ultrasonically examining remotely located welds in cast stainless steel nuclear steam supply systems.

BACKGROUND OF THE INVENTION

FIG. 1 illustrates a nuclear steam supply system 20 in accordance with the prior art. As known in the art, the system 20 includes a reactor vessel 22 with a core 24. The system 20 also includes a set of coolant loops 26A–26D. Each coolant loop 26 includes a steam generator 28 and an associated reactor coolant pump 30. Each steam generator 28 includes a feedwater inlet 32 and a steam outlet 34.

The operation of a nuclear steam supply system 20 is well known in the art. Coolant leaving the reactor vessel 22 enters a steam generator 28 where it imparts its heat to a working fluid which exits as steam through a steam outlet 34. The steam is then used to drive a turbine (not shown) to produce electricity. The coolant leaves the steam generator 28 via the reactor coolant pump 30 and is pumped back to the reactor vessel 22.

The present invention is directed toward the maintenance of reactor coolant pumps 30 associated with nuclear steam supply systems. FIG. 2 is a cut-away view of a prior art reactor coolant pump 30. The reactor coolant pump 30 includes a pump shaft 40 connected to an impeller 42. A seal housing 44 surrounds the pump shaft 40. The seal housing includes a set of seal injection lines or pipes 46A, 46B.

The reactor coolant pump 30 also includes a casing 48. A set of cooling lines or pipes 50A, 50B pass through the casing 48 and into a thermal barrier 52. The casing 48 and thermal barrier 52 are formed of cast stainless steel.

FIG. 3 is a top view of a cooling line 50 passing into the casing 48. FIG. 4 illustrates the seal injection line 46 terminating in a thermal barrier 52. A weld 60 is used to connect the seal injection line 46 to the thermal barrier 52.

The present invention is directed toward identifying a flaw 62 associated with a weld 60. The flaw may be in many forms, for example, a crack or an incomplete weld penetration. The flaw may be in a cooling line 50, a seal injection line 46, or any other remote location. The invention is most useful in relation to cast stainless steel components associated with nuclear steam supply systems.

There are no known prior art techniques for identifying flaws in attachments to reactor coolant pumps of nuclear steam supply system coolant loops. More particularly, there are no known techniques for identifying flaws in seal injection lines and cooling lines of reactor coolant pumps. The present practice is to wait for a failure and then shutdown the plant. Repairs and welds are then made during shutdown. The expense associated with an unplanned shutdown of this type is typically about $500,000 per day. Thus, it would be highly desirable to provide a technique for detecting flaws in remotely located nuclear steam supply system components. Such a technique would save critical operation time and prevent unscheduled plant outages.

It is difficult to identify defects of the type described above for a number of reasons. First, the defects are remotely located. Therefore, a special apparatus must be contrived to reach the remote location. Another problem is that the seal injection lines 46 and cooling lines 50 are connected to cast stainless steel components.

Conventional ultrasonic examination of such components is not possible for the following reasons. First, the properties of the cast stainless steel material from which the thermal barrier is fabricated are not conducive to the transmission of ultrasonic energy due to large gain structure, ultrasonic beam redirection, and ultrasonic scattering. Second, access to the thermal barrier for ultrasonic examination is limited by component geometry. Third, the welds are typically not examined due to inherent reflectors formed during fabrication of the weld joint. Fourth, the orientation of the crack is not conducive to a conventional examination procedure, even if the material properties would permit ultrasonic transmission and subsequent reflection from the crack face.

Cast stainless steel material typically consists of large, randomly orientated grain structure that tends to scatter and otherwise disperse ultrasonic energy. The nuclear power industry has spent a great deal of money trying to identify ultrasonic examination techniques for cast stainless steel material, with very limited success. Present techniques for ultrasonic examination of cast stainless steel material is unreliable, at best. The most promising results, although very limited, have been obtained by using low frequency, large diameter, dual-element ultrasonic transducers. The available access to the thermal barrier is inadequate for this size of probe. In addition, even if the ultrasonic energy were to reach the crack location, the ultrasonic wave length would be too large (with low resolution) for efficient reflection from the small crack face. The beam size of conventional probes is also larger than this particular weld and would result in an ineffective examination.

In view of the foregoing, it would be highly desirable to provide an ultrasonic examination technique to detect remotely located flaws in nuclear steam supply systems prior to leakage. Such a technique would allow repair of the flaws during scheduled refueling outage, instead of during unplanned outages.

SUMMARY OF THE INVENTION

An apparatus for ultrasonically examining a weld in a nuclear steam supply system includes an elongated guide rod for positioning within a pipe of the nuclear steam supply system. The pipe may be, for example, a seal injection line or cooling line of a reactor coolant pump. An ultrasonic transducer is positioned at an end of the elongated guide rod. A collapsible shoe encloses the ultrasonic transducer. The collapsible shoe includes a biasing mechanism to allow the collapsible shoe to pass through the pipe while the pipe is at a first circumference and while the pipe is at a second circumference. The collapsible shoe continuously contacts the pipe to establish ultrasonic coupling for the ultrasonic transducer.

The invention can detect weld flaws without the need of passing the ultrasonic beam through the complex grain structure of the cast stainless steel. The invention can be used to identify weld flaws during scheduled outages so that unexpected damaging weld leaks and concomitant plant outages can be avoided.

BRIEF DESCRIPTION OF THE DRAWINGS

For a better understanding of the invention, reference should be made to the following detailed description taken in conjunction with the accompanying drawings, in which:

FIG. 1 is a perspective view of a nuclear steam supply system in accordance with the prior art.

FIG. 2 is a cut-away view of a reactor coolant pump used in the system of FIG. 1.

FIG. 3 is a top view of a cooling line entering a reactor coolant pump.

FIG. 4 is a side view of a weld connecting a reactor coolant pump seal injection line and a thermal barrier.

FIG. 5 is a side view of an ultrasonic examination device in accordance with the invention.

FIG. 6 Illustrates the ultrasonic examination device of FIG. 5 being used to identify a remotely located flaw in a reactor coolant pump.

Like reference numerals refer to corresponding parts throughout the drawings.

DETAILED DESCRIPTION OF THE INVENTION

FIG. 5 is a side view of an ultrasonic examination device 70 of the invention. The device 70 includes an elongated guide rod 72 and an ultrasonic transducer 74. The ultrasonic transducer 74 is positioned within a collapsible shoe 76.

The collapsible shoe 76 includes a biasing mechanism (1) to allow the collapsible shoe to pass through pipe segments of different circumferences, and (2) to establish ultrasonic coupling for the ultrasonic transducer at a weld location in the pipe. As used herein, the term "pipe segments" refers to a single pipe with different circumferences or attached pipes with different circumferences.

The elongated guide rod 72 is pushed through a pipe until the collapsible shoe 76 is at a weld location to be examined. Preferably, the elongated guide rod 72 includes measurement indicia to assess how far the elongated guide rod 72 has been pushed into a pipe.

Once at the weld location, the ultrasonic transducer produces an ultrasonic signal indicative of the geometry of the remotely located weld. The signal is passed over line 75 and is then processed in a standard manner, as discussed below.

As indicated above, the collapsible shoe 76 includes a biasing mechanism that may be implemented with a first shoe half 78 and a second shoe half 80. Preferably, each shoe half includes tapered ends 82. The shoe halves include aligned bias chambers 84. Springs 86 or other biasing elements are placed within the biasing chambers 84. Thus, the collapsible shoe 76, shown in an expanded state, can be collapsed into a collapsed state. A transducer well 88 accommodates the transducer 74 when the collapsible shoe 76 is in the collapsed state.

The springs 86 operate to provide tight ultrasonic coupling during examinations. That is, the springs 86 force the collapsible shoe 76 against the pipe at the weld location. Typically, the collapsible shoe 76 will pass through a narrow circumference pipe segment (e.g., 1.3 inches) before reaching the weld location. The collapsible shoe 76 will be in a collapsed state in the narrow circumference pipe segment. When the collapsible shoe is at the weld location, it is typically at a wide circumference pipe segment (e.g., 1.5 inches). At this location, the biasing mechanism presses the collapsible shoe 76 into an expanded state such that it is forced against the pipe to insure ultrasonic coupling. The tapered ends 82 allow the collapsible shoe 76 to easily transition from pipe segments with different circumferences.

The ultrasonic exam device 70 of FIG. 5 is used in connection with seal injection lines 46 and cooling lines 50 of a reactor coolant pump 30. By way of example, FIG. 6 illustrates the ultrasonic exam device 70 positioned in a seal injection line 46 of a reactor coolant pump 30. The figure illustrates the placement of the device 70 inside the seal injection line 46, with the ultrasonic beam 90 passing through the wall of the line 46, through the weld metal 60, and interacting with a flaw 62 in the thermal barrier 52. Observe that this ultrasonic examination technique is accomplished without passing through the complex grain structure of the cast stainless steel of the thermal barrier 52.

The invention has been implemented to produce 45° and 60° longitudinal waves and a 45° shear wave. The various angles and modes of propagation are achieved by altering the angle of the transducer 74 in the collapsible shoe 76. Snell's Law is then applied using the acoustic velocity of the thermal barrier 52 and the acoustic velocity of the material of the shoe 76 to calculate the angles for each mode of propagation.

The invention has been implemented with a ¼ inch diameter transducer 74. Frequencies of 2.25 Mhz for shear and 3.5 Mhz for longitudinal waves have been successfully used. The guide rod preferably includes a scale or other measurement indicia to identify the distance to the beam exit point.

The examination process preferably includes the following steps. First, the device 70 is calibrated such that the instrument screen display represents a linear metal path distance. The device 70 is then inserted through the line opening and is positioned at the start of the examination zone. The device 70 is then moved through the examination zone to evaluate the signal display. The device 70 is then withdrawn to the start of the examination zone, is rotated, and then the process is repeated. The extent of rotation is such that a minimum of 10% overlap is achieved within the examination volume.

Signal characteristics and sound path distances are evaluated to determine whether the weld area contains flaws in the form of cracks or incomplete penetration. Standard ultrasound signal processing techniques may be used. However, the following factors should be considered when discriminating between cracks and incomplete penetrations. Only maximum amplitude signals obtained within the examination zone require evaluation. Only signals having sound paths of between 0.25" and 0.65" for the 45° probes and 0.4" to 0.95" for the 60° probe require evaluation. Signals outside of these sound path ranges are outside of the suspected crack area.

A crack signal has a longer sound path distance than does the signal from an incomplete penetration, due to the location of the crack being on the far side of the weld as compared to the incomplete penetration being at the weld root. The change in metal path distance will decrease with decreasing crack depths. The crack signal contains more facets than the incomplete penetration signal. The signal amplitude will vary as a function of the size of the flaw and the orientation of the flaw with respect to the transducer.

Once a flaw is identified, standard techniques are used to repair the flaw. For example, the flaw may be repaired by grinding it out and rewelding.

While the invention has been disclosed in reference to the repair of seal injection lines and cooling lines in reactor coolant pumps, those skilled in the art will appreciate that the invention is also applicable to other remote geometries, especially those that have associated cast stainless steel components.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed, obviously many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for ultrasonically examining a weld in a nuclear steam supply system, comprising:

an elongated guide rod;

a collapsible shoe positioned on an end of said elongated guide rod, said collapsible shoe including a first shoe half aligned with a second shoe half, said shoe halves movable between an expanded state and a collapsed state;

an ultrasonic transducer positioned within said collapsible shoe;

a biasing mechanism biasing said shoe halves continuously against the inner wall of a pipe at a weld location in said pipe, said biasing mechanism comprising two or more aligned biasing elements, said biasing elements being placed within aligned bias chambers in said shoe halves, said biasing elements pressing said collapsible shoe into said expanded state such that is forced against said pipe to ensure ultrasonic coupling between said pipe and said ultrasonic transducer through said collapsible shoe; and a transducer well located in said first shoe half, said transducer well accommodating said ultrasonic transducer when said shoe halves are in said collapsed state.

2. The apparatus of claim 1 wherein said pipe is connected to a cast stainless steel component of said nuclear steam supply system.

3. The apparatus of claim 2 wherein said pipe is formed in a reactor coolant pump of said nuclear steam supply system.

4. The apparatus of claim 3 wherein said pipe is a seal injection line.

5. The apparatus of claim 3 wherein said pipe is a coolant line.

6. The apparatus of claim 1 wherein said elongated guide rod includes measurement indicia indicating the distance said elongated rod is placed in said pipe.

7. The apparatus of claim 1 wherein said collapsible shoe includes tapered ends to facilitate transition between a first pipe circumference and a second pipe circumference.

8. The apparatus of claim 1 wherein the angle at which said ultrasonic transducer is positioned within said collapsible shoe may be altered to produce longitudinal waves between 45° and 60°.

9. The apparatus of claim 1 wherein the angle at which said ultrasonic transducer is positioned within said collapsible shoe may be altered to produce shear waves at 45°.

10. The apparatus of claim 1 wherein said two or more biasing elements are springs.

* * * * *